United States Patent [19]  [11] 4,316,892
Jones  [45] Feb. 23, 1982

[54] 2,6-C-DIMETHYLTYROSINE[1]-D-AMINO ACID[2]-ε-AMINO CAPROIC AND γ AMINOBUTYRIC ACID[5] DERIVATIVES OF METHIONINE ENKEPHALIN

[75] Inventor: David A. Jones, Evanston, Ill.
[73] Assignee: G. D. Searle & Co., Skokie, Ill.
[21] Appl. No.: 202,920
[22] Filed: Nov. 3, 1980
[51] Int. Cl.$^3$ .................. A61K 37/00; C07C 103/52
[52] U.S. Cl. .................. 424/177; 260/112.5 E
[58] Field of Search .................. 260/112.5 E; 424/177

[56] References Cited
U.S. PATENT DOCUMENTS
4,178,371 12/1979 Morgan .................. 260/112.5 E Primary Examiner—Delbert R. Phillips
Attorney, Agent, or Firm—James G. Passé

[57] ABSTRACT

An enkephalin derivative represented by the formula (±)
H-2,6-C-diMeTyr-(D)X-Gly-Phe-N(CH$_2$)$_m$COOR wherein: X is methionine, alanine or nor-leucine; m is 3 or 5; and R is selected from the group consisting of hydrogen, lower alkyl or -NR$_2$R$_3$ wherein R$_2$ and R$_3$ are the same or different members of the group consisting of hydrogen and lower alkyl, wherein the (±) refers to the compound shown, its mirror image or a mixture of racemates; or the pharmaceutically acceptable salts thereof. The compounds are useful as analgesic agents.

12 Claims, No Drawings

2,6-C-DIMETHYLTYROSINE[1]-D-AMINO ACID[2]-ε-AMINO CAPROIC AND γ AMINOBUTYRIC ACID[5] DERIVATIVES OF METHIONINE ENKEPHALIN

BACKGROUND OF THE INVENTION

In 1975, a pentapeptide, methionine enkephalin, was reported by Hughes et al. Nature, 258,577(1975). This peptide is found in many areas of the brain where it appears to act as a neurotransmitter of neuromodulator in a central pain suppressant system. The natural peptide binds stereospecifically to partially purified brain opiate receptor cites see, for example, Bradbury et al., Nature 260,793(1976). The natural peptide is also highly active in bioassays for opiate activity but exhibits only weak, fleeting analgesic activity when injected directly into the brain of the rat see for example Belluzi et al., Nature, 260,625(1976).

In order to overcome the lack of in vivo activity, a number of investigators have made numerous modifications in the methionine enkephalin structure, such as substituting the glycine in the 2-position with a D-amino acid, N-methylation of the 1-tyrosine, substituting the 4-phenylalanine with, for example methyl or halo, modifying the C-terminus, etc. to produce enkephalin derivatives of varying properties and potencies.

The present invention provides new enkephalin derivatives and their pharmaceutically acceptable salts which approach the potency of morphine as analgesic agents by both oral and parenteral routes of administration.

SUMMARY OF THE INVENTION

The present invention provides novel derivatives of methionine enkephalin, 2,6-C-dimethyltyrosyl-D-methionylglycyl-phenylalanyl-γ-aminobutyric acid and derivatives and 2,6-C-dimethyltyrosyl-D-methionyl-glycyl-phenylalanylcaproic acid and derivatives and the pharmaceutically acceptable salts thereof. The compounds are useful as analgesic agents.

DETAILED DESCRIPTION OF PREFERRED EMBODIMENTS

The enkephalin derivatives of the present invention are represented by the formula

(±)H-2,6-C-diMeTyr-(D)X-Gly-Phe-N(CH$_2$)$_m$COOR wherein: X is methionine, alanine or nor-leucine; m is 3 or 5; and R is hydrogen, lower alkyl or —NR$_2$R$_3$; wherein R$_2$ and R$_3$ are the same or different members of the group consisting of hydrogen or lower alkyl; wherein the (±) refers to the compound shown, its mirror image or a mixture of racemates; or the pharmaceutically acceptable salts thereof.

In the above formula, "C-diMe" stands for the dimethyl substitution on the aromatic ring of tyrosine. Prior art substitutions of tyrosine have been N-substitutions, and it has been found the C-substitution unexpectedly increases the activity of the compounds.

All amino acid residues identified herein are in the natural or L-configuration unless otherwise specified, with the exception of glycine which has no center of symmetry, and standard abbreviations for the amino acid residues have been used.

The dimethyltyrosine residue may be in the L, D or DL configuration.

The term "lower alkyl" refers to C$_1$–C$_6$ straight or branched chain alkyl radicals, i.e. methyl, ethyl, n-propyl, iso-propyl, n-butyl, tert-butyl, n-hexyl, etc.

The term "pharmaceutically acceptable salts", as used herein, refers to the non-toxic acid addition salts which are generally prepared either in situ or by reacting a compound of this invention with the desired organic or inorganic acid according to methods well known in the art. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, tosylate, napsylate, etc.

The analgesic activity for the compounds of the present invention was first established in the hot plate assay and mouse PBQ writhing assay.

The compounds of the present invention can be administered by either oral or parenteral routes of aministration to relieve pain in mammalian patients suffering therefrom in oral dosages of from 0.5 to 5 mg/kg of body weight and from 0.05 to 3 mg/kg of body weight daily, preferably in divided dosages, i.e. every 4 to 6 hours as needed for relief of pain.

The following examples further illustrate the present invention.

EXAMPLE 1

Preparation of tert-butyloxycarbonyl-phenylalanylmethyl-ε-aminocaproate

To a cold solution of 2.65 g (10.0 mmole) of tert-butyloxycarbonyl (Boc)-phenylalanine and 2.00 g (11.0 mmole) of methyl caproate hydrochloride in 25 ml of methylene chloride were added 1.25 ml (11.2 mmole) of dicyclohexylcarbodiimide and 1.25 ml (1.10 mmole) of N-methyl morpholine. The reaction mixture was stirred for 30 minutes at room temperature and then refrigerated for several days.

The dicyclohexylurea formed in the reaction was filtered and the filtrate extracted with water several times, dried over anhydrous magnesium sulfate and finally filtered and evaporated. The resulting oil soon solidified to give a quantitative yield of product. TLC[chloroform:methanol:acetic acid:water (83:15:1:1v/v/v/v]-R$_f$0.85. The structure was confirmed by NMR.

EXAMPLE 2

Preparation of tert-butyloxycarbonyl-phenylalanylmethyl-γ-aminobutyrate

The title compound was prepared in the idential manner as in Example 1 from 2.65 of Boc-Phe, 1.69 g (11.0 mmole) of methyl-γ-aminobutyrate hydrochloride salt, 1.25 ml of N-methylmorpholine and 2.27 g (11.0 mmole) of dicyclohexylcarbodiimide in 25 ml of methylene chloride, reacted for 24 hours, to provide a quantitative yield of product (TLC in the above solvent system, R$_f$ 0.84).

EXAMPLE 3

Preparation of phenylalanyl-methyl-ε-amino caproate hydrochloride

Tert-butyloxycarbonyl-phenylalanyl-methyl-ε-amino caproate (10.0 mmole) was dissolved in 37 ml of glacial acetic acide and treated with 18 ml of 5.6 N hydrochloric acid in dioxane for 20 minutes at room temperature. The solvents were evaporated and anhydrous ether added to form a precipitate. The cold precipitate was filtered and washed with ether, then dried in vacuo at 65° C. for 3 hours to yield 2.79 g of product (84.8% yield).

EXAMPLE 4

Preparation of phenylalanyl-methyl-γ-aminobutyrate hydrochloride

The procedure of Example 3 was followed, using identical amounts of materials to yield 2.85 g of product (98.4% yield).

EXAMPLE 5

Preparation of Boc-glycyl-phenylalanyl-methyl-ε-amino caproate

To 2.45 g (7.45 mmole) of the dipeptide of Example 2 and 2.04 g (8.57 mmole, 15% excess) of Boc-gly-2,4,5-trichlorophenyl ester (OCP) in 15 ml of dimethylformamide was added 0.85 ml (7.65 mmole) of N-methylmorpholine and the reaction mixture was allowed to stand at room temperature for 48 hours. Addition of 175 ml of cold, 5% potassium bisulfate gave a gummy precipitate which was extracted (3×50 ml) into ethyl acetate. The combined organic layers were washed with water, then brine and dried over anhydrous magnesium sulfate and, after filtering, evaporated to leave an oil.

The product was purified via low pressure liquid chromatography using silica gel and eluting with a 100% chloroform to 100% ethyl acetate linear gradient. The weight of oily product was 3.17 g (94.6% yield). TLC[chloroformethyl acetate (1:1 v/v)]$R_f$0.09.

EXAMPLE 6

Preparation of Boc-glycyl-phenylalanyl-methyl-γ-aminobutyrate

The above named compound was prepared from 2.55 g (8.49 mmole) of the dipeptide of Example 4, 3.47 g (9.77 mmole, 15% excess) of Boc-Gly-OCP and 1.1 ml (9.9 mmole) of N-methylmorpholine in 17 ml of dimethylformamide following the method of Example 5. Following workup as in Example 5, the product was purified by low pressure liquid chromatography using a 95% chloroform/5% Skellysolve B to 100% ethyl acetate linear gradient on a 25×100 mm silica gel column to yield 2.52 g (70.4%) of product. TLC[chloroform:methanol:acetic acid:water (83:15:1:1 v/v/v/v)]$R_f$ 0.74; TLC chloroformethyl acetate (1:1 v/v) $R_f$0.06.

EXAMPLE 7

Preparatiom of Glycyl-phenylalanyl-methyl-ε-amino caproate hydrochloride

The compound of Example 5(3.17 g, 7.05 mmole) was dissolved in 26 ml of acetic acid and treated at room temperature with 13 ml of acetic acid and treated at room temperature with 13 ml of 5.7 M hydrochloric acid/dioxane for 25 minutes. The solvents were evaporated and the resulting crystalline solid was washed with ether and then dried in vacuo at 60° C. for 2½ hours to yield 2.68 g (98.6% yield). TLC chloroform:methanol:acetic acid:water (83:15:1:1 v/v/v/v) gave one spot, $R_f$0.09.

EXAMPLE 8

Preparation of glycyl-phenylalanyl methyl-γ-aminobutyrate hydrochloride

The Boc-peptide of Example 6(2.52 g, 5.99 mmole) was dissolved in 22 ml of acetic acid and treated according to the method of Example 7 with 10.7 ml of 5.6 N hydrochloric acid in dioxane. After workup and drying in vacuo at 55° C. for 3 hours, a 98.6% yield of product (2.14 g) was obtained. Elemental analysis showed it to be a ¼ hydrate. TLC [methanol-acetic acid-water-chloroform(15:1:1:83 v/v/v/v)], $R_f$ 0.07 (homogeneous).

EXAMPLE 9

Preparation of Boc-(DL)-2,6,C-dimethyltyrosyl-(D)-methionyl glycyl-phenylalanyl-methyl-γ-aminobutyrate A solution of (DL) Boc-2,6-C-dimethyltyrosyl-(D)-methionine (1.37 g, 3.05 mmole) in 18.5 ml of dimethylformamide and 0.72 ml (6.48 mmole) of N-methylmorphine was cooled to −60° C. and 0.42 ml(3.20 mmole, 5% excess) of isobutylchloroformate was added all at once. The solution was stirred for 10 minutes while the temperature climbed to −50° C., after which 1.21 g(3.35 mmole) of the tripeptide hydrochloride of Example 8 in 9 ml of dimethylformamide was added over a 20 minute period, keeping the temperature at less than −° C. The reaction mixture was stirred at about −10° C. for 30 minutes, then allowed to warm to room temperature and maintained at room temperature fo 20 hours.

The reaction mixture was then added to 300 ml of cold, 5% potassium bisulfate to give a white precipitate which was filtered, washed with water and dried to give 1.97 g(86.8% yield) of product. TLC[chloroform:methanol:acetic acid:water(83.15:1:1 v/v/v/v]-two spots of equal intensity (diastereomers) at $R_f$ 0.70 and 0.76.

EXAMPLE 10

Preparation of Boc-(DL)-2,6-C-dimethyltyrosyl-(D)-methionylglycyl-phenylalanyl-methylε-amino caproate The title compound was prepared from 1.29 g (3.35 mole) of the tripeptide hydrochloride of Example 7 and the same molar excesses of Boc-(DL)2,6-C-dimethyltyrosyl-(D) methanione, N-methylmorpholine and isobutylchloroformate and solvent were added in the same manner as in Example 9. Work up as in Example 9 gave 2.19 g of product (93.2%). TLC in the solvent system of Example 9 gave two spots of equal intensity, $R_f$0.64 and 0.72.

EXAMPLE 11

Preparation of (DL)2,6-C-dimethyltyrosyl-(D)-methionylglycyl-phenylalanyl-methyl-γ-aminobutyrate hydrochloride The protected peptide of Example 9 (1.97 g, 2.65 mmole) was treated for 20 minutes at room temperature in 10 ml of acetic acid and 5 ml of 5 M hydrochloric acid in dioxane, and the solvents were evaporated. The addition of ether and trituration afforded a powder which was filtered, washed with ether and dried in vacuo at 60° C. for 3½ hours to yield 1.81 g(96.8% yield of product as a hydrochloride 1½ H$_2$O, M.W. 707.28.[α]$_D^{25}$+5.0° (c 0.1, methanol). Elemental analysis and NMR analysis confirmed the structure.

EXAMPLE 12

Preparation of (DL)-2,6-C-dimethyltyrosyl-(D)-methanionylglycyl-phenylalanyl-methyl caproate hydrochloride The protected pentapeptide of Example 10 (2.19 g, 2.84 mmole) was treated as above with hydrochloric acid in dioxane to give, after drying at 60° C. for 2½ hours in vacuo, 1.89 g(91.9%) of product as a hydrochloride 1–1.2 H$_2$O.[α]$_D^{25}$+3.0° (c 0.1, methanol). Elemental analysis and NMR analysis confirmed the structure.

It will be apparent to those skilled in the art that the acids, amides and other lower akyl esters of this invention can be readily obtained by selection of the appropriate intermediates. Representative compounds of the present invention include but are not limited to:

(DL)-2,6-C-dimethyltyrosyl-(D)-methionyl-glycyl-phenylalanyl-ε-amino caproic acid;

(DL)-2,6-C-dimethyltyrosyl-(D)-methionyl-glycyl-phenylalanyl-γ-aminobutyric acid;

(DL)-2,6-C-dimethyltyrosyl-(D)-methionyl-glycyl-phenylalanyl-iso-propyl ε-amino caproate hydrobromide;

(DL)-2,6-C-dimethyltyrosyl-(D)-methionyl-glycyl-phenylalanyl-N-methyl ε-amino caproamide; etc.

The present invention includes within its scope pharmaceutical compositions comprising, as an active ingredient, at least one of the compound of formula I in association with a pharmaceutical carrier of diluent. The compounds of this invention can be administered by oral, parenteral, nasal, vaginal, rectal or sublingual routes of administration and can be formulated in dosage forms appropriate for each route of administration.

Solid dosage forms for oral administration include capsules, tablets, pills, powders and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides, inert diluents, such compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsion. Examples of non-aqueous solvents or vehicles are propylene glycol, vegetable oils, such as olive oil, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into compositions. They can also be manufactured in the form of sterile solid compositions which can be dissolved in sterile water, or some other sterile injectable medium immediately before use.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 0.5 to 5 mg/kg of body weight daily are administered to mammals to obtain effective relief from pain.

I claim:

1. An enkephalin derivative represented by the formula

wherein: X is methionine, alanine or nor-leucine; m is 3 or 5; and R is selected from the group consisting of hydrogen, lower alkyl or —NR$_2$R$_3$; wherein R$_2$ and R$_3$ are the same or different members of the group consisting of hydrogen and lower alkyl; wherein the (±) refers to the compound shown, its mirror image or a mixture of racemates; or the pharmaceutically acceptable salts thereof.

2. A compound of claim 1 wherein m is 3.

3. A compound of claim 1 wherein m is 3 and R is hydrogen.

4. A compound of claim 2 wherein R is lower alkyl.

5. A compound of claim 4: (DL)-2,6-C-dimethyltyrosyl-(D)methionyl-glycyl-phenylalanyl-methyl-γ-aminobutyrate or a pharmaceutically acceptable salt thereof.

6. A compound of claim 2 wherein R is NR$_2$R$_3$.

7. A compound of claim 1 wherein m is 5.

8. A compound of claim 7 wherein R is hydrogen.

9. A compound of claim 7 wherein R is NR$_2$N$_3$.

10. A compound of claim 7 wherein R is lower alkyl.

11. A compound of claim 10: (DL)-2,6-C-dimethyltyrosyl-(D)methionyl-glycyl-phenylalanyl-methylε-amino caproate or a pharmaceutically acceptable salt thereof.

12. A method of treating pain comprising administering a therapeutically effective amount of a compound of claim 1 to a mammalian patient suffering from pain.

* * * * *